United States Patent [19]

Zhu et al.

[11] Patent Number: 5,423,814
[45] Date of Patent: Jun. 13, 1995

[54] ENDOSCOPIC BIPOLAR COAGULATION DEVICE

[75] Inventors: Yong H. Zhu, Loma Linda; Wolff M. Kirsch, Redlands, both of Calif.; Zhen-Sheng Tang, Shanghai, China

[73] Assignee: Loma Linda University Medical Center

[21] Appl. No.: 68,137

[22] Filed: May 25, 1993

Related U.S. Application Data

[63] Continuation of Ser. No. 981,862, Nov. 25, 1992, abandoned, which is a continuation of Ser. No. 880,757, May 8, 1992, Pat. No. 5,293,863.

[51] Int. Cl.$^6$ ............................................. A61B 17/39
[52] U.S. Cl. ............................... 606/46; 606/41; 606/47; 606/48; 606/51
[58] Field of Search ............................... 606/41, 45–52, 606/205–208; 607/115, 116

[56] References Cited

U.S. PATENT DOCUMENTS

| | | |
|---|---|---|
| 1,770,653 | 7/1930 | Molony . |
| 3,685,518 | 8/1972 | Beuerie et al. . |
| 3,920,021 | 11/1975 | Hiltebrandt . |
| 4,003,380 | 1/1977 | Wien . |
| 4,074,718 | 2/1978 | Morrison, Jr. . |
| 4,307,720 | 12/1981 | Weber, Jr. . |
| 4,492,231 | 1/1985 | Auth . |
| 4,543,090 | 9/1985 | McCoy . |
| 4,753,223 | 6/1988 | Bremer . |
| 5,013,312 | 5/1991 | Parins et al. . |
| 5,085,657 | 2/1992 | Ben-Simhon . |
| 5,125,896 | 6/1992 | Hojeibane . |
| 5,152,748 | 10/1992 | Chastagner . |
| 5,192,280 | 3/1993 | Parins .................... 606/50 |
| 5,197,962 | 3/1993 | Sansom et al. . |
| 5,209,747 | 5/1993 | Knoepfler ............... 606/205 |
| 5,277,696 | 1/1994 | Hagen . |
| 5,282,799 | 2/1994 | Rydell . |
| 5,290,285 | 3/1994 | Kirwan, Jr. . |
| 5,290,286 | 3/1994 | Parins . |
| 5,295,990 | 3/1994 | Levin . |

Primary Examiner—Stephen C. Pellegrino
Assistant Examiner—Michael Peffley
Attorney, Agent, or Firm—Knobbe, Martens, Olson & Bear

[57] ABSTRACT

A bipolar coagulation device suitable for use in endoscopic surgery is disclosed which reduces the adhesion of tissue to the electrodes and enables the user to clean the electrodes during the procedure without removal from the body. Bipolar electrocautery forceps are located at the distal end of a sheath suitable for use in endoscopic surgery. The tips of the forceps are manipulated using controls located at the control end of the sheath which remains outside the patient's body. The tips of the forceps are made of material having phosphorous in combination with metals of high thermal conductivity, which reduces the adhesion of tissue during cauterization. In addition, the device has a cleaner which acts to free the forceps of any adhering debris. This cleaning can be done inside the patient's body, without the need for any additional instrumentation. In a preferred embodiment, the tips of the bipolar coagulation device can also be pivoted to an angularly disposed position.

17 Claims, 7 Drawing Sheets

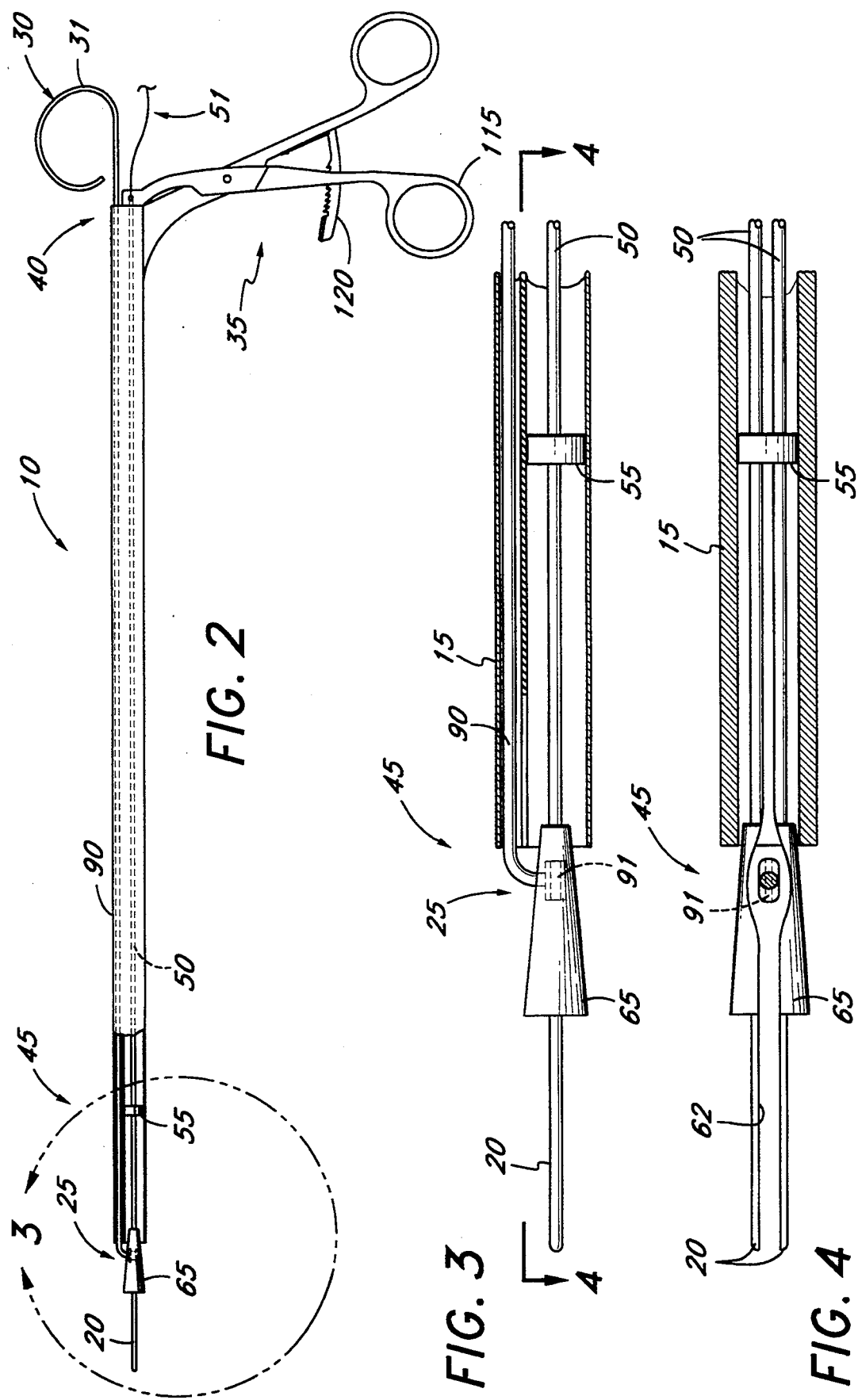

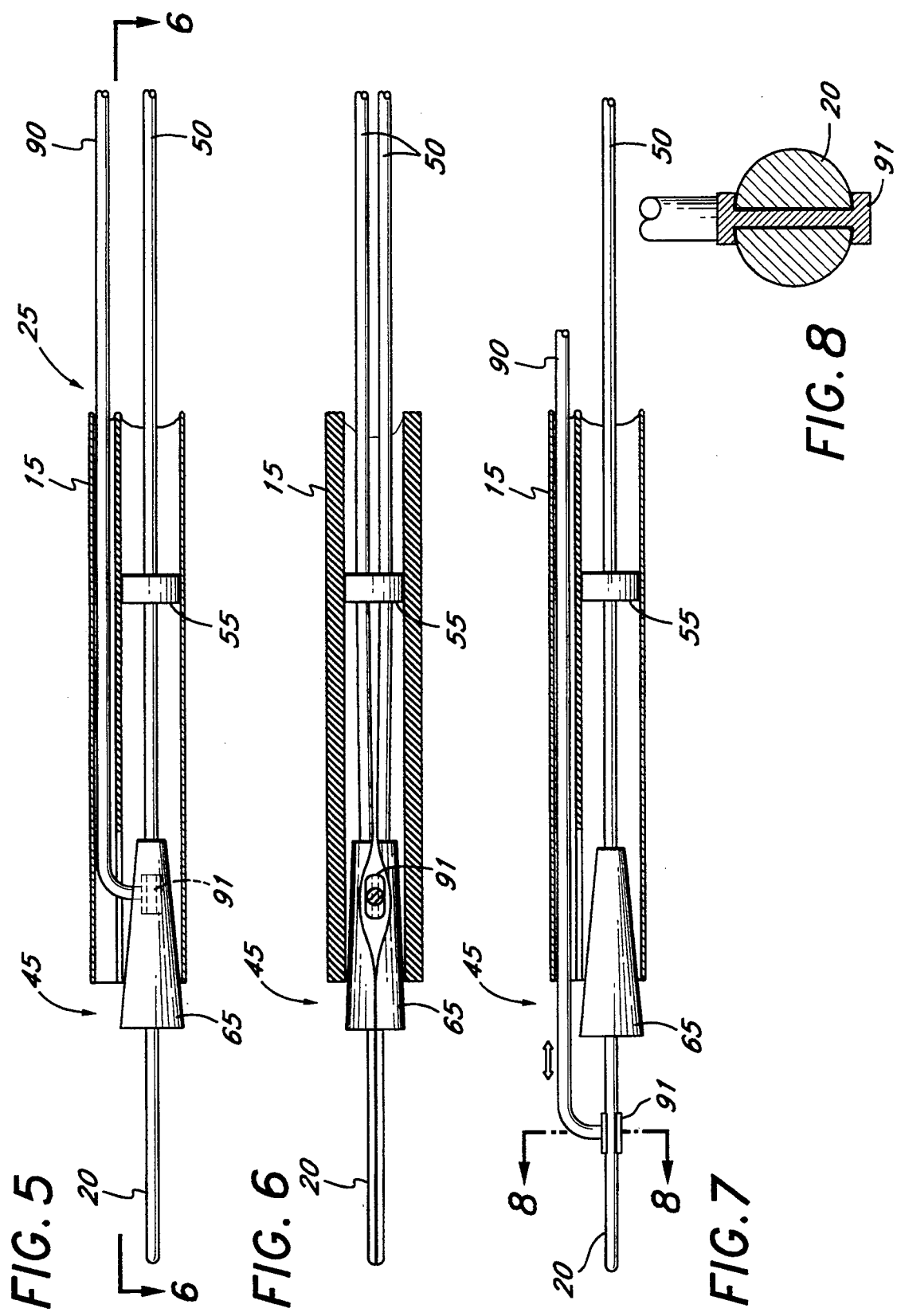

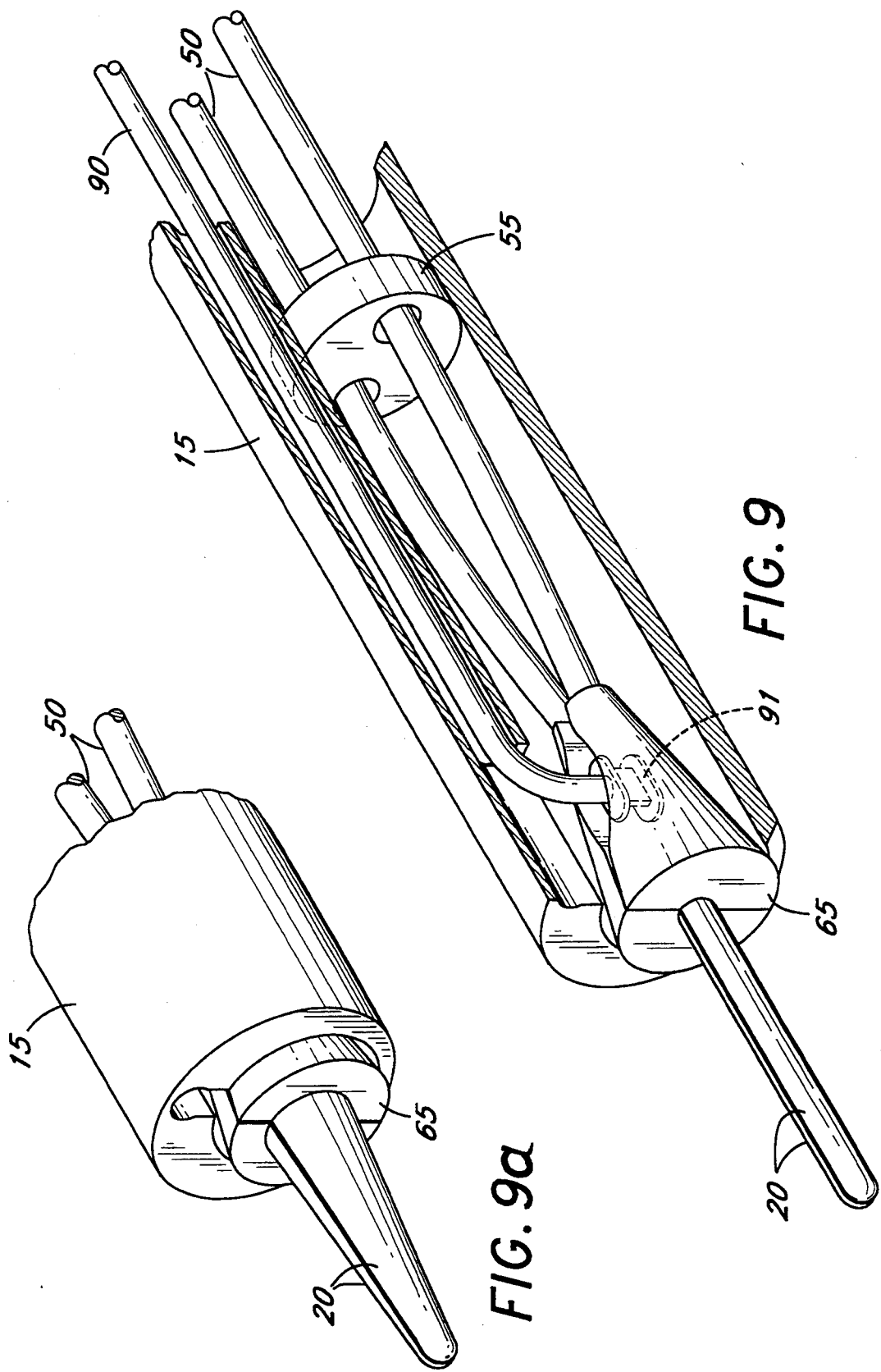

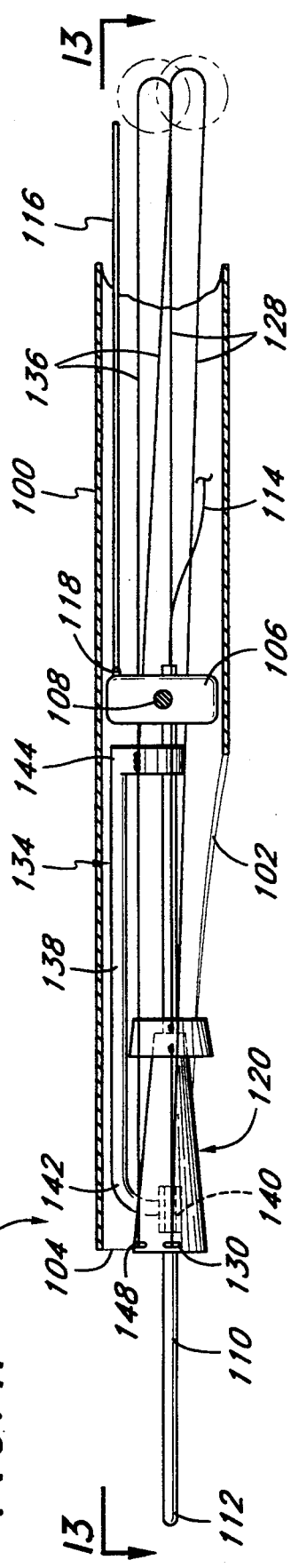

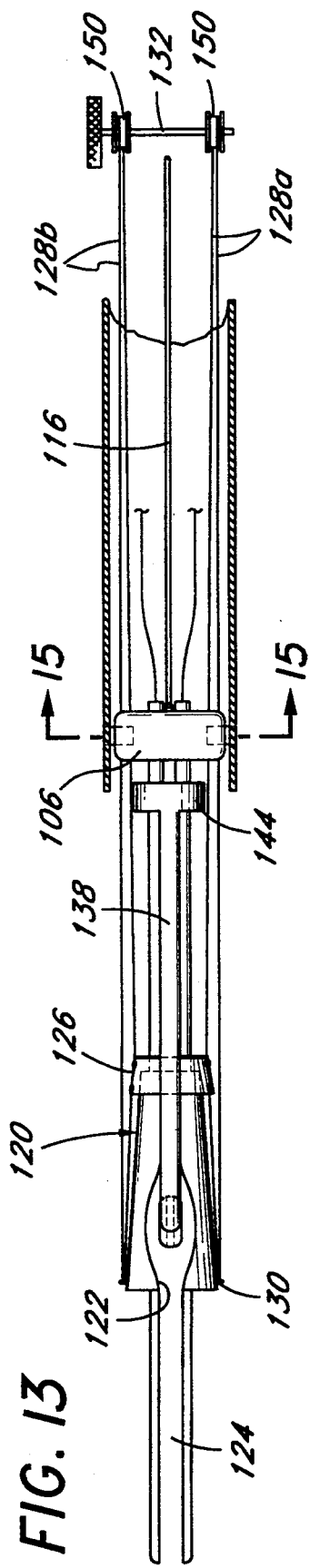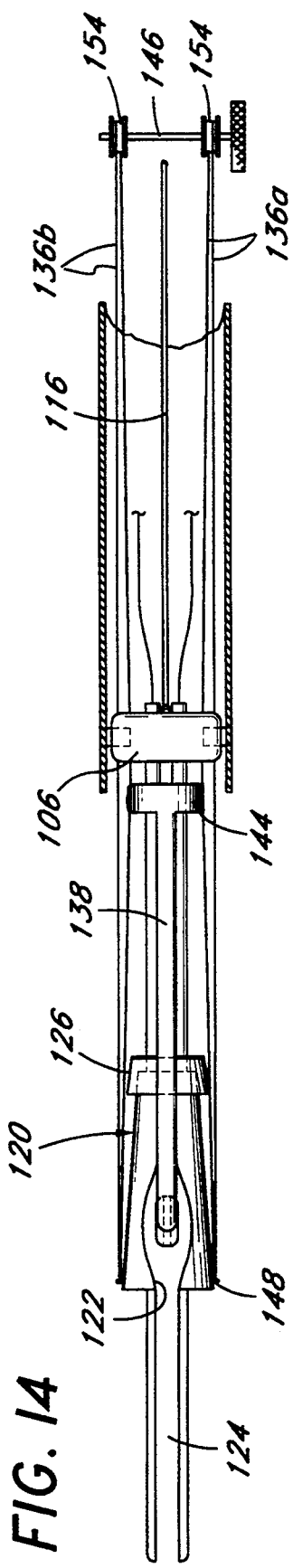

ENDOSCOPIC BIPOLAR COAGULATION DEVICE

RELATED APPLICATIONS

This application is a continuation of U.S. patent application Ser. No. 981,862, filed Nov. 25, 1992, now abandoned, which is a continuation in part of U.S. patent application Ser. No. 880,757, filed May 8, 1992, now U.S. Pat. No. 5,293,863, entitled BLADED ENDOSCOPIC RETRACTOR.

FIELD OF THE INVENTION

The present invention relates to electrocautery devices used in surgery. Specifically, the invention relates to a bipolar endoscopic coagulation device having articulating tips (i.e., electrodes) to which the adhesion of tissue is minimized, and from which the user can remove any tissue debris during the endoscopic surgical procedure without removal of the device.

BACKGROUND OF THE INVENTION

The field of endoscopic surgery has been advancing rapidly in recent years. In this form of surgery, procedures are performed inside the body of a patient using instruments inserted through small incisions or ports in the body. The surgery is performed with the aid of an endoscope, which is a thin, tube-like instrument featuring a light source, a viewing lens, and/or various other attachments such as irrigators, scissors, snares, retractors, or forceps.

This form of surgery allows internal visualization of the body structure without the necessity of excessive dissection of tissue. Typical endoscopes often are in the 5–12 mm diameter range and thus require only very small incisions to insert them into the body. Endoscopic surgery has developed rapidly because of the numerous benefits arising in favor of the patient. Since there is only a small incision to permit entrance of the endoscope, endoscopic surgery results in less trauma to the body and faster patient recovery.

Electrosurgery has been an accepted surgical tool for at least six decades. The use of an electric current to control bleeding, known as "electrocautery", replaced thermal cautery because of its speed and effectiveness. Electrocautery is based on the observation that a high frequency alternating current can be passed through the body with no untoward effects other than heat production. Use of an intermittent high frequency current results in blood coagulation within tissues with little or no cutting effect on the tissues themselves.

Electrosurgical devices can be monopolar or bipolar. In a monopolar system, the electrical current passes from a smaller "active" electrode located at the tip of the device, through the tissue, to a dispersive electrode, also known as a patient plate. The dispersive electrode has a large contact area. Because of its broad exposure area, temperature rise is insignificant. In contrast, the active electrode is typically 1 mm in size, thus concentrating the dissipated electrical current to a highly confined region with a resulting rapid rise in tissue temperature.

Electrosurgery performed in open, that is, non-endoscopic surgery is associated with significant hazards. These include the risk of explosive anaesthetic agents, or flammable bowel gas, faulty grounding contacts, or short circuiting. One of the hazards frequently associated with the use of monopolar electrosurgery is the inadvertent reduction of area at the dispersive electrode, which has resulted, in some cases, in severe burns to the patient's body.

Many of these grounding plate and non-conductive tissue thermal injuries are thought to be reduced by the use of bipolar cautery. With bipolar cautery, both the active and ground electrodes are placed at the tips of the forceps, and thus current flows only between the two active electrodes.

This bipolar method, however, has a number of significant disadvantages. These include tissue dehydration, increased resistance, and uncontrolled heating, leading to tissue vaporization, charring, and actual explosions. A major disadvantage is the rapid heating, burning, and sticking of tissue. This results in the need for frequent cleaning of the bipolar forceps, which slows the operation, and in fact, results in ineffective and inefficient coagulation. In addition, when tissue adheres to the tips of the forceps, withdrawal of forceps from the coagulated tissue can cause inadvertent tearing and hemorrhaging.

Stainless steel has been the metal of choice for the production of both monopolar and bipolar coagulation forceps. Steel, however, is a poor thermal conductor, and its use results in uncontrolled heating at the tips of the forceps and adhesion of tissue. Attempts to prevent adhesion have included various coatings of the stainless steel forceps, but these attempts have not been successful.

The techniques of endoscopic surgery and electrocautery have been combined, resulting in endoscopic devices capable of coagulating tissue. However, additional disadvantages arise during endoscopic procedures because the electrocauterization is done inside the patient's body through an endosurgical port, with no direct access by the surgeon to the site of the procedure. The forceps must be cleaned outside the patient's body, or through the use of a separate device inserted into the body. This slows the procedure and increases trauma to the patient.

Bipolar coagulation has never been completely accepted by surgeons practicing laparoscopic surgery, that is, endoscopic surgery within the abdominal cavity. The monopolar coagulating electrode is considered to be the optimal tool, but its use is complicated by inadvertent injury to the bowel or adjacent structures by short circuiting, as well as tissue oxidation and adherence to the monopolar tips. In addition, the use of monopolar endoscopic electrocautery devices can interfere with radio-frequency waves which are often used to assist the surgeon in visualizing internal body structures.

There is therefore a need for a bipolar coagulation device suitable for use in laparoscopic and other forms of endoscopic surgery, capable of disseminating heat away from the tips of the forceps to reduce uncontrolled heating, charring and sticking of the tissue during surgery, and a mechanism for cleaning the tips of the forceps quickly and easily during the endoscopic procedure.

SUMMARY OF THE INVENTION

The present invention provides an apparatus and method for improved endoscopic electrocauterization procedures. The invention reduces tissue adhesion during coagulation, and provides for the cleaning of the device during the procedure without removal of the device from the patient.

Coagulation is accomplished with the present invention through the use of an electric current which travels across the tips/electrodes of a bipolar forceps, and through the tissue held between the tips of the forceps. The forceps are at the distal end of a tubular sheath designed for use in endoscopic procedures.

In one embodiment of the present invention, the electrocautery forceps are comprised of a pair of electrically conductive rods which pass from one end of the sheath to the other. At the insertion or distal end of the sheath, these rods end in bipolar electrocautery forceps. In a preferred embodiment, the tips of these forceps in cross-section have a flat tissue contacting area and rounded outer edges.

The tips are comprised of material which exhibit good properties for non-adherence of tissue during coagulation. Although an explanation for the advantages of the present invention is not completely understood at the present time, it is believed that the use of phosphorous in combination with high heat transfer metals results in a polymerization which inhibits sticking. Preferably, this tip material contains from 4.75% to 15.5% silver and up to 7.5% phosphorous, with the remainder being copper. Use of a copper-silver-phosphorous alloy results in the forceps tips having excellent electrical and thermal conductivity, while also being strong and corrosion resistant.

The bipolar coagulation device includes a wedge on at least one of the rods of the electrocautery forceps which provides for actuation of the tips when coagulation is desired. The wedge acts to bring the tips of the forceps together when either the rods are pulled back into the sheath, or when the sheath is pushed forward over the rods. Either motion causes the tapered end of the wedge to fit inside the distal end of the sheath which results in a camming action thus forcing the tips of the forceps to come together. Typically, the tips/electrodes are brought together so as to engage the tissue to be cauterized. Following cauterization, movement of the tips of the forceps away from the distal end of the sheath causes the tips of the forceps to separate because of their normal outward structural spring bias.

At the proximal or control end of the sheath, which remains outside the patient's body during surgery, handles are used to manipulate the tips of the forceps. By pulling the handle connected to the rods away from the handle connected to the sheath, the tapered end of the wedge is brought into the distal end of the sheath, and the tips of the forceps are forced together. By pushing the handle connected to the rods forward, the wedge is moved away from the distal end of the sheath, and the tips of the forceps separate. Once separated, the tips can be positioned on either side of the tissue to be coagulated. Once properly positioned, the tips can then be brought together, thus capturing the tissue between the tips.

The rods of the forceps are connected to an electric source, in a manner well known in the art, at the proximal end of the sheath. When current is activated (by, for example, activation of a foot pedal) the current travels down one of the rods and into the cathode tip of the bipolar forceps. The current travels through the tissue held between the tips of the forceps, causing it to coagulate, and then to the anode, whereupon the circuit is completed.

Another advantage of the present invention is that the bipolar electrocautery device has an attached cleaner. This cleaner is comprised of a rod extending through the sheath from one end to the other. At the distal end of the sheath, the rod ends in a tip which is configured to conform to and follow the tips of the electrocautery forceps. This tip can be made of various materials, including, for example, plastic or metal. Use of a metal tip results in improved cleaning, however, safety measures must be taken to ensure that current cannot be activated during the cleaning process.

When it is desired to clean the tips of the forceps, the handle of the cleaner is pushed forward, sliding the cleaner along the flat and curved surfaces of the tips, freeing the tips of any debris adhering to the surfaces. The handle of the cleaner is then pulled back, once again sliding the cleaner across the surfaces of the tips of the forceps. This movement can be repeated, if necessary, until the tips are free of all adhering debris. A significant advantage of the present invention is that this cleaning of the forceps can be done inside the patient's body, without the need for removing the forceps or the need for any additional surgical instruments.

In a further preferred embodiment of the present invention, the coagulation device includes a mechanism for pivoting the electrocautery forceps to an angularly disposed position relative to a tubular insertion sheath. The pivotable coagulation device includes a mechanism for manipulating the electrocautery forceps together or separating them apart, for linearly actuating a clearing rod to clean the forceps tips, and for tilting or angling the electrocautery forceps at the distal end of the tubular sheath to contact tissue areas off the axis of the tubular sheath. Advantageously, the cleaning tip may be actuated at any angular position of the electrocautery forceps. The body of the tubular sheath has an opening along one side at its distal end to allow angular or bending movement of the electrocautery forceps downwardly, away from the tubular body.

In accordance with the coagulation device having pivotable forceps, the proximal ends of the electrocautery forceps are mounted to a disk-shaped tilt control member inside the tubular sheath. The tilt control member includes a pin pivotable about the interior wall of the tubular sheath defining a tilt axis for the electrocautery forceps. To effect tilting of the forceps, a rigid elongated tilt rod attaches to a position on the proximal face of the disk-shaped tilt control member enabling the tilt rod to cause rotation of the tilt control member about the tilt axis. Pushing or pulling of the rigid tilt rod causes the tilt control member to pivot about the pin and therefore angle the attached electrocautery forceps through the opening in the sheath.

An electrocautery forceps movement control member surrounds a pair of half-cone-shaped camming members formed integrally with the forceps halfway between the tilt control member and the extreme distal tip of the forceps. The coagulation control member comprises a short tubular sleeve capable of sliding longitudinally over the camming members. The camming members have a wide end toward the distal tip of the forceps and a narrower end towards the proximal direction. The coagulation sleeve causes the tips of the forceps to close when slid over the camming members in the distal direction. When the sleeve is subsequently retracted in the proximal direction, the forceps tips are allowed to open due to their normal outward structural spring bias.

The coagulation sleeve is preferably longitudinally displaced to open or close the forceps tips via a pair of control wires connected to the coagulation sleeve and ultimately manipulated at a handle mechanism on the proximal end of the tubular sheath. The control wires attach to two sides of the coagulation sleeve to apply symmetric pulling forces and extend in either direction to apply force in both directions. A continuous loop wire on each side attaches to the coagulation sleeve and extends proximally, passing through the tilt control member and to the handle, whereupon the wire is looped around a shaft to extend distally through the tilt control member, reversing directions through a pulley or eyelet at the distal end of one of the camming members, to terminate back at the coagulation sleeve. The continuous loop configuration of the control wire allows movement in both longitudinal directions when the shaft at the control handle is turned. In addition, the flexible nature of the control wires allows the electrocautery forceps to be angled at the tilt control member without affecting the actuation of the electrocautery forceps.

In a similar manner as the coagulation sleeve, a cleaning tip member may be displaced longitudinally in order to clean the electrocautery forceps tips via a second pair of control wires. The cleaning rod includes an elongated shaft portion having a cleaning tip formed by a 90° bend at the distal end thereof and normally disposed within a recess between the half cone-shaped camming members. The proximal end of the rod includes a ring-shaped guide member sized to travel along and around the electrocautery forceps. The cleaning rod may slide distally so that the cleaning tip scrapes the inside edges of the electrocautery forceps completely to the distal tips. At the same time, the guide member slides distally from the tilt control member to a position adjacent the camming members.

A continuous control wire on each side for symmetrical force application controls the longitudinal displacement of the control rod. In this respect, the control wire mounted to the guide member extends through an aperture in the tilt control member proximally to wrap around a second actuation shaft at the handle, and thereafter distally through the tilt control member and through a pulley or eyelet at the distal edge of the camming member to reverse direction and terminate at the guide member. Rotation of the second actuation shaft causes sliding movement of the cleaning rod. Advantageously, the cleaning rod may be actuated with the electrocautery forceps in a straight or angled orientation due to the flexibility of the control wires.

The endoscopic bipolar electrocautery forceps of the present invention significantly reduce the risks associated with monopolar electrosurgery, such as explosions, short circuiting, and burning of the patient's body. This is due to the fact that both the active and ground electrodes are placed at the tips of the forceps, eliminating the need for the current to travel great distances inside the patient's body before reaching the dispersive electrode.

The present invention also provides significant advantages over current bipolar electrosurgery methods by using forceps made of a material having small amounts of phosphorous in combination with metals having high thermal conductivity. This reduces the occurrence of uncontrolled heating, charring, and adhesion of the tissue to the tips of the forceps during the coagulation procedure.

In addition, the ability to clean the tips of the forceps during the procedure, within the body of the patient, and without the need for any additional instrumentation and without removal from the body is an important advantage of the present invention. Further, the ability to pivot the electrocautery forceps inside the patient's body provides a significant advantage when positioning and using the forceps inside the patient's body. The present endoscopic bipolar coagulation device is also small enough to be easily introduced into the body through a single endoscopic port, resulting in reduced trauma to the patient.

Thus, the endoscopic bipolar coagulation device of the present invention provides a very advantageous solution to the problems associated with prior endoscopic electrocautery procedures.

BRIEF DESCRIPTION OF THE DRAWINGS

FIG. 2 is a side view of the endoscopic bipolar coagulation device of the present invention.

FIG. 3 is an enlarged view of the distal end of the device of the present invention indicated by circle 3—3 in FIG. 2, with the tips of the forceps shown in an extended, separated position, the cleaner shown in a retracted position, and the sheath shown in cross-section.

FIG. 4 is a top plan cross-sectional view taken through the line 4—4 of FIG. 3, showing the tips of the forceps in the same position as in FIG. 3.

FIG. 5 is an enlarged view of the distal end of the device similar to FIG. 3, showing the tips of the forceps in a retracted, closed position as they would be during electrocauterization, and the cleaner in a retracted position.

FIG. 6 is a top plan cross-sectional view similar to FIG. 4, showing the tips of the forceps in the same retracted, closed position as FIG. 5.

FIG. 7 is an enlarged view of the distal end of the device similar to FIG. 5, except that the cleaner is shown in an extended position as during the cleaning of the tips.

FIG. 8 is a cross-sectional view of the cleaner and tips of the forceps taken along line 8—8 indicated in FIG. 7.

FIG. 9 is a perspective view of the distal end of the device of the present invention with the sheath partially broken away to reveal the placement of the cleaning device relative to the forceps.

FIG. 9a is a perspective view of an alternate embodiment of the forceps of the present invention provide enhanced heat transfer to prevent sticking.

FIG. 11 is a side view of the distal end of a second embodiment of the present invention, showing the mechanism for bending the electrocautery forceps.

FIG. 12 is a side view of the distal end of the second embodiment of the present invention similar to FIG. 11, except that the tips of the forceps are shown in an angled position.

FIG. 13 is a top plan cross-sectional view of the second embodiment of the present invention, with the tips of the forceps shown in an extended, separated position, the cleaner shown in a retracted position, the sheath shown in cross-section, and the second pair of control wires removed.

FIG. 14 is a top plan cross sectional view of the second embodiment of the present invention similar to FIG. 13, except that the second pair of control wires are present, and the first pair of control wires are removed.

FIG. 15 is a cross-sectional view of the tilt control member taken along line 15—15 indicated in FIG. 13.

DETAILED DESCRIPTION OF THE INVENTION

Figure 1:
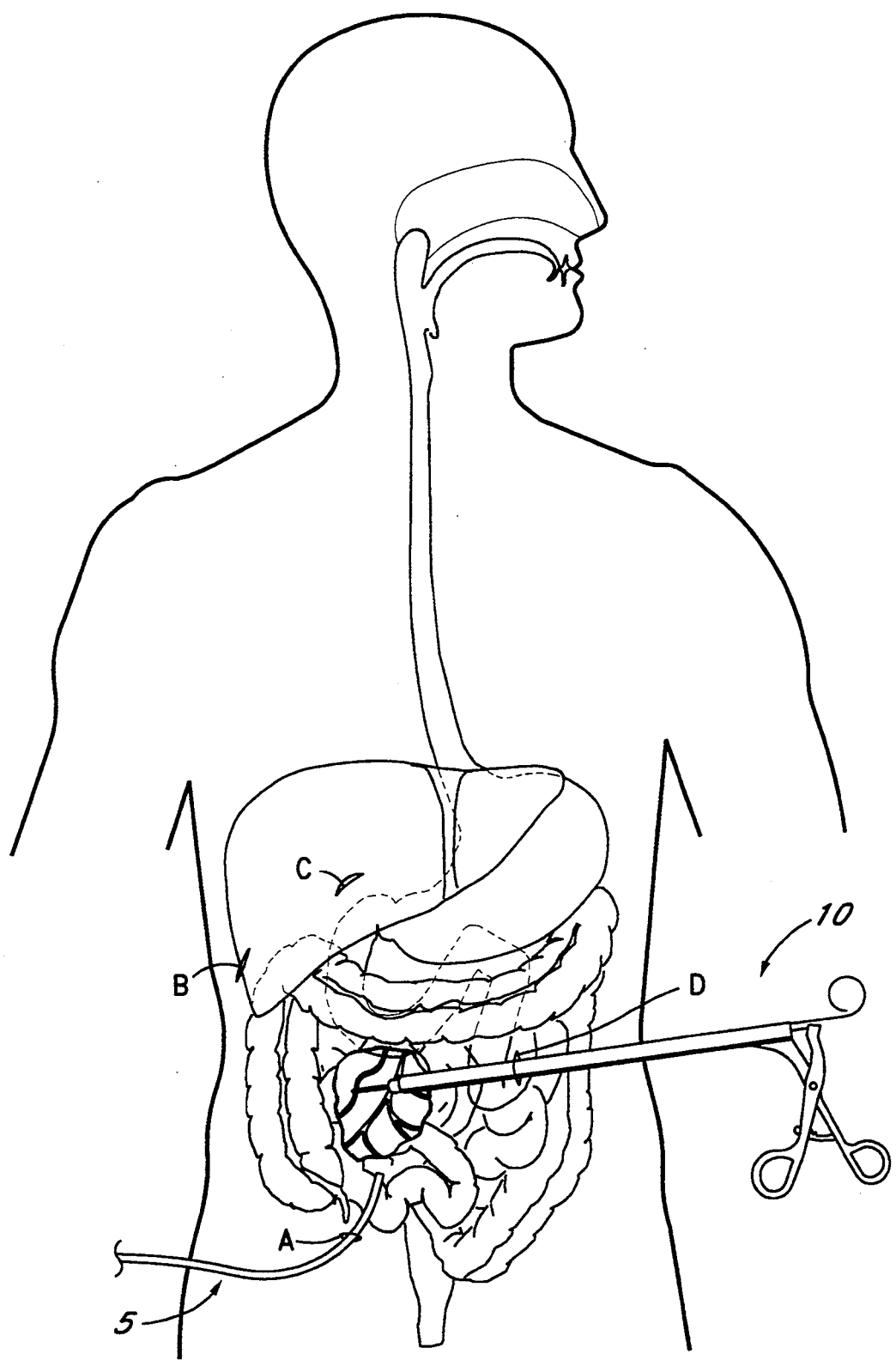
FIG. 1 is a schematic view illustrating the manner in which the endoscopic bipolar coagulation device of the present invention may be inserted through a small surgical port for use in endoscopic surgery.

Referring first to FIG. 1, there is shown a schematic view of a patient undergoing endoscopic surgery. A small endosurgical port A is shown, through which an endoscope 5 is inserted. This allows the surgeon to view the internal organs and tissue in the surgical area. Other surgical devices (not shown) may be inserted through similar surgical ports B and C in order to perform the desired procedure.

The endoscopic bipolar coagulation device 10 of the present invention is shown inserted through yet another port D so as to be in the surgical region. Thus, the electrocautery device can be used to coagulate tissue safely and easily during surgery. It should be noted, however, that the principles of the present invention are not limited to any particular surgical procedure but may be applied to a wide variety of procedures and applications, including open surgery.

Construction of the Device

Referring to FIG. 2, there is shown one embodiment of the endoscopic bipolar coagulation device 10 of the present invention. The device 10 has a distal cauterizing or insertion end 45 (circled with a dotted line in FIG. 2) and an opposite proximal or control end 40, the two ends being joined by an elongate sheath 15. At the distal end, the sheath 15 has forceps 20 and a cleaner 25 extending therefrom which are manipulable by various controls 30 and 35 located at the proximal end. As will become apparent below, the forceps 20 comprise tips/electrodes used to engage the tissue to be coagulated, while the cleaner 25 can be used to remove any tissue that may have adhered to the forceps 20. A wedge-like device 65 serves to activate the forceps 20 in cooperation with the sheath, as explained below in more detail. As illustrated, the sheath 15 of the endoscopic electrocautery device 10 is a tube. The sheath 15 may be shaped differently, however, a circular cross-section is preferred since it is most easily inserted into a cannula. The outer diameter of the sheath 15 is preferably minimized so that the incision required to insert the endoscopic electrocautery device and the trauma to the patient's body are also minimized. The length of the sheath 15 is primarily dependent upon the type of procedure in which the electrocautery device is to be used. The sheath 15 is preferably made of a material, such as stainless steel, which will remain free from degradation, is easily sterilized, and is biocompatible.

Two electrically conductive rods 50 are encased within the sheath 15. As shown in FIG. 2, at the distal end of the sheath 45, these rods 50 terminate in forceps 20 having bipolar electrodes at their tips. As will be discussed below in more detail in connection with FIGS. 9 and 10, the shape of the rods 50 and the position of the rods within a disk 55 of insulating material positioned inside the sheath 15 prevents the rods 50 from contacting one another inside the sheath 15.

FIG. 2 illustrates a preferred embodiment wherein the rods 50 are connected by means of an electrical connection 51 to an electrical source (not shown) at the proximal end of the sheath 40. As will be readily apparent to those of ordinary skill in the art, this connection 51 can be made in several different ways. As will be explained below in connection with the operation of the invention, upon activation of the current, the current travels down one of the rods 50 to the electrodes at the tips of the forceps. The current travels between the electrodes of the bipolar forceps 20, through the tissue held between the tips of the forceps, causing the tissue to coagulate.

Still referring to FIG. 2, behind or proximal of each tip of the forceps is a wedge 65 which acts as a cam to bring the tips of the forceps 20 together as the rods 50 are pulled toward the proximal end of the sheath 40. In an alternate embodiment, (not shown) the sheath 15 is moved toward the distal end of the forceps 20. This camming action will be discussed in more detail below in connection with FIGS. 3–6.

Handles 110, 115 are located outside the proximal end of the sheath 40 as shown in FIG. 2. The handles 110, 115 as illustrated are elongated and are of a dimension sufficient to permit manipulation by hand. Each handle 110, 115 is preferably made from stainless steel. The handles 110, 115 could of course be made of plastic or other durable material. Handle 110 is connected securely to the sheath 111. Handle 115 is connected to the rods 50 which end in the forceps 20. As will be explained in more detail below in connection with the operation of the present invention, handle 115 causes the rods 50 to be drawn in a proximal direction. However, other means for manipulating the device are possible which are within the scope of the present invention.

FIG. 2 also illustrates a notched member 120 extending from handle 115 towards handle 110. The notched member 120 is slightly curved and lies directly alongside handle 110. The notches in the notched member 120 are engaged by a pin (not shown) extending outwardly from handle 110. In this manner, handle 110, and its corresponding forceps tips 20, may be locked into any position using the pin and notch lock.

As shown in FIG. 2, at its proximal end 30, the cleaner 25 ends in a handle 31 which remains outside the proximal end of the sheath 40 and outside the patient's body. The handle 31 is of a dimension sufficient to allow manipulation by hand. The handle 31 is preferably made of stainless steel, but could, of course, be made of plastic or any durable material.

FIGS. 3 and 4 illustrate the distal end of the device of the present invention, with the tips of the forceps 20 and the wedges 65 in their extended, open position. This position is achieved upon the relative motion of the wedges 65 away from the distal end of the sheath 45. As a result of the shape of the rods 50 and their position within the sheath 15, discussed below in more detail in connection with FIGS. 9 and 10, the tips of the forceps 20 separate once the tips 20 are moved beyond the distal end of the sheath 45. The tip of the cleaner 91 remains in its retracted position behind the tips of the forceps 20, between the wedges 65.

As illustrated in FIG. 4, the tips of the forceps 20 are preferably rounded, and each tip has a flat surface 62 facing the other tip where tissue may be contacted. The tips 20 are comprised of a material having very high thermal conductivity. In a preferred embodiment, the tips are comprised of an alloy containing from 4.75% to 15.5% silver and up to 7.5% phosphorous, with the remainder being copper. More preferably, the alloy comprises 15% silver, 80% copper, and 5% phosphorous. This results in heat being drawn away from the tips of the tissue contacting areas of the forceps 62. Thus, rapid overheating, charring and adhesion of the tissue to the forceps 20 can be avoided.

FIGS. 5 and 6 illustrate the tips of the forceps 20 and the wedges 65 in their retracted, closed position. As can be seen, each wedge 65 is tapered at its proximal end to fit within the sheath 15, and widens to a point where it no longer fits within the sheath. As a result of the shape of the rods 50 and their position within the sheath 15, discussed below in more detail in connection with FIGS. 9 and 10, upon the relative motion of the wedges 65 toward the distal end of the sheath 45, the tips of the forceps 20 are brought together. The tip of the cleaner 91 remains in its retracted position behind the tips of the forceps 20, between the wedges 65.

As illustrated in FIGS. 5 and 6, each wedge 65 is configured in the shape of a half-cone, the flat surface of one half-cone facing the flat surface of the other half-cone, and the rounded surfaces facing outward. As will be readily apparent to one of ordinary skill in the art, other shapes may be used to bring the tips of the forceps 20 together in a similar camming action.

FIG. 7 illustrates the cleaner 25 in its extended position, cleaning the surfaces of the tips of the forceps 20. As can be seen, the cleaner 25 comprises a rod 90 which lies inside the length of the sheath 15 and a tip 91. As the rod of the cleaner 90 moves forward toward the distal end of the sheath 45, the tip of the cleaner 91 moves along the flat and rounded surfaces of the tips of the forceps 20. As shown in the cross-sectional view of FIG. 8, the cleaner tip 91 is configured such that it follows the surfaces of the tips of the forceps 20. Thus, cleaning occurs not only along the flat surfaces of the forceps 20 which touches the tissue to be cauterized, but also engages the outer rounded edges of the tips for more effective cleaning.

Turning now to FIG. 9, the placement of the cleaner 90 when not in use relative to the tips of the forceps 20 can be seen. In its retracted position, the tip of the cleaner 91 rests behind, or proximal of, the tips of the forceps 20, in a hollowed-out area between the wedges 65.

Figure 10:
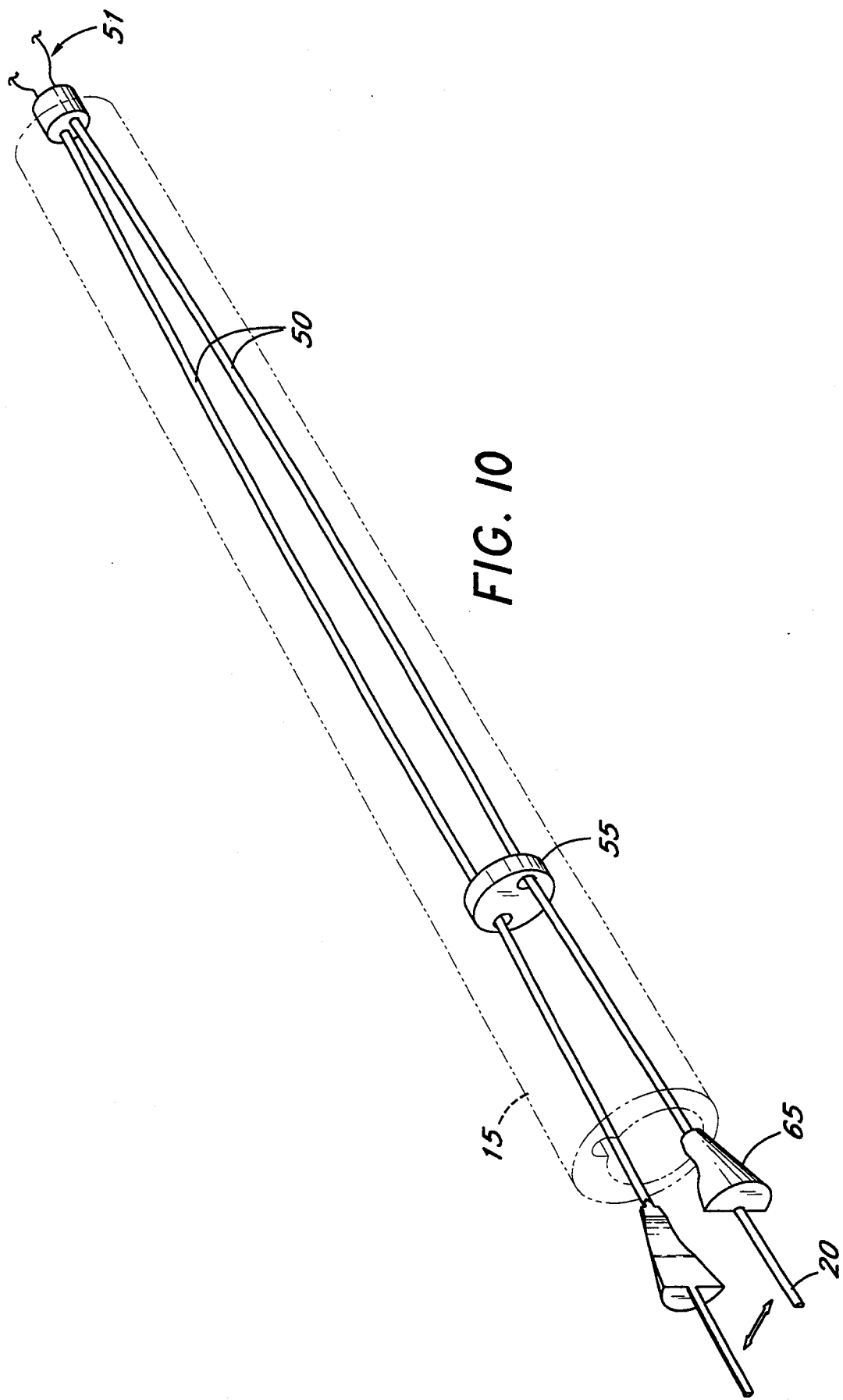
FIG. 10 is a perspective view of the electrically conductive rods of the present invention, showing their construction within the sheath.

The configuration of the rods within the sheath is illustrated in FIGS. 9 and 10. The rods 50 are forked such that they bow out from one another inside the sheath 15. In addition, each rod 50 fits within a hole in a disk 55 of insulating material positioned inside the sheath 15. This configuration results in the creation of a bias spring force. Thus, when the wedges 65 are positioned beyond the distal end of the sheath 45, the tips of the forceps 20 separate. When the wedges 65 are positioned within the distal end of the sheath 45, the tips of the forceps 20 are forced together. In addition, this configuration prevents the rods 50 from contacting one another inside the sheath 15.

Because of this bias spring force which tends to cause the forceps 20 to separate from one another, an effective method for cleaning can be accomplished. That is, referring again to FIG. 7, it will be noted that tips 91 of the cleaner 25 engage the tips of the forceps 20 when the forceps 20 are brought together. Thus, the wedges 65, as shown in FIG. 7, are drawn into the sheath 15 in order to counteract the bias spring force acting on the forceps 20, thereby ensuring a firm frictional engagement between the cleaning tips 91 and the forceps 20. This frictional engagement results in more effective cleaning. It will be noted that, since the cleaning tips 91 reside, when not in use, within the wedges 65, it is necessary to advance the cleaner 25 to its cleaning position adjacent the forceps 20 while the forceps are separated (as shown in FIG. 4), and then to retract the wedges 65 in order to bring the forceps 20 together against the cleaning tips 91 for cleaning.

As will be readily apparent to those of ordinary skill in the art, other configurations are possible which will result in the creation of a bias spring force and in isolating the rods from one another within the sheath.

Configuration and Material of the Tips

The tips of the bipolar forceps 20 are comprised of material having good properties for non-adherence of tissue during cauterization. Preferably, this material contains from 4.75% to 15.5% silver and up to 7.5% phosphorous, with the remainder being copper. Alloys containing over 6% phosphorous are difficult to fabricate, however, and the forms available are limited. More preferably, the alloy used is comprised of 80% copper, 15% silver, and 5% phosphorous. Use of a copper-silver-phosphorous alloy reduces the adhesion of tissue to the tips, and results in the forceps tips 20 having excellent electrical and thermal conductivity, while also being strong and corrosion resistant.

Alternatively, the copper-silver-phosphorous alloy can be used to coat the surface of forceps tips comprised of other material such as stainless steel. This results in the tips having a higher electrical and thermal conductivity and improved physical properties than would be present using the steel tips alone.

Without wishing to be bound by any particular theory, it is believed that use of a copper-silver alloy containing a relatively small percentage of phosphorous results in an improved surface of the electrocautery forceps. Phosphorous is commonly used as a flux in copper brazing alloys. A flux is used to prevent the oxidation of the filler metal and of the surfaces being joined during the heating. The flux also dissolves oxides that may form during the heating process. Phosphorous also aids in the wetting and flowing of the brazing alloy on the surfaces to be joined.

It is believed that the phosphorous in the tips is oxidized at high temperatures and polymerizes, forming a poly-phosphate compound which prevents the other metals from contacting the tissue during coagulation. This polymeric surface prevents the adhesion of tissue to the tips.

In addition, it is also believed that the configuration of the tips of the forceps 20 may enhance the non-stick properties of the forceps. As shown in FIG. 9a, in an alternate embodiment of the forceps 20, the tips thereof may be thickened in order to provide a heat sink during coagulation. It is believed that the thickness and shape of the tips promotes heat transfer away from the tissue contacting surfaces of the tips, thus reducing the occurrence of uncontrolled heating, charring, and adhesion of the tissue to the tips during the coagulation procedure.

Operation

Referring now to FIGS. 2-9, the operation of the endoscopic electrocautery device 10 as used during surgery will now be described. The device 10 is inserted into the patient's body. This is normally accomplished by inserting a cannula into the body and then sliding the electrocautery device 10 through the cannula. When the device 10 is initially inserted, the forceps 20 and cleaner 25 should be in their non-use positions as shown in FIG. 9. The tips of the forceps 20 should be closed with the tip of the cleaner 91 resting behind the tips of the forceps 20 and the wedges 65 resting partially inside the distal end of the sheath 45.

Once the electrocautery device 10 is in the body, it may be properly aligned and operated. Once the device 10 is in the desired location, handle 115 is pulled toward handle 110 along the notched member 120. The wedges 65 are pushed forward past the distal end of the sheath 45, causing the tips of the forceps 20 to separate (FIGS. 3 and 4). The tips 20 are then placed on opposite sides of the tissue to be cauterized. The tips 20 are brought together by pushing handle 115 away from handle 110, causing the wedges 65 to be pulled back inside the distal end of the sheath 45, or by sliding the sheath 45 forward toward the distal end of the tips 20 (FIGS. 5 and 6). Once the tips 20 are together, the user activates a current. The current flows through one of the rods 50 inside the sheath 15 to the cathode, passes between the cathode and the anode in the tips of the forceps 20 resulting in cauterization of the tissue, and then flows down the other rod 50 inside the sheath 15. The tips of the forceps 20 are then separated, and the cauterized tissue is released.

Should the user desire to clean the tips of the forceps 20 after cauterization, he grasps the handle of the cleaner 31 and moves it toward the distal end of the sheath 45. As illustrated in FIG. 7, this causes the tip of the cleaner 91 to slide between the tips of the forceps 20, freeing them of any debris. The handle 31 can then be pulled back toward the proximal end of the sheath 40, bringing the cleaner tip 91 to its resting position behind the tips of the forceps 20. This movement can be repeated several times, in effect scrubbing the forceps tips 20 clean.

Once the surgical procedure has been completed, the electrocautery device 10 is removed from the patient's body. With the tip of the cleaner 91 in its non-use position, handle 115 is pushed away from handle 110. Pushing handle 115 in this direction causes the rods 50 to slide toward the distal end of the sheath 45, pulling the wedges 65 into the distal end of the sheath 45, causing the tips of the forceps 20 to come together just outside the distal end of the sheath 45 as shown in FIG. 9. At this time, the electrocautery device 10 may be removed from the body.

A Second Embodiment of the Device

In another embodiment of the coagulation device 10, the distal portion 45 comprises a mechanism for angling the electrocautery forceps while still allowing the forceps to be opened and closed, and the cleaning rod to be actuated. With reference to FIG. 11, the distal portion 45 of the coagulation device comprises a body or tubular sheath 100 having a lower elongated aperture 102 extending in the proximal direction a short distance from a distal end 104. A tilt control member 106 rotatably mounts to the interior of the tubular sheath 100 via a pair of pivot pins 108. A pair of rigid electrocautery electrodes or forceps 110 rigidly attach to the tilt control member 106 and extend distally therefrom to terminate in electrocautery tips 112 distal from the end of the tubular sheath 100. The electrodes or forceps 110 are mounted in the tilt control member 106 so that they are biased slightly apart. Flexible electrical conducting leads 114 extending from the tilt control member 106 proximally to a handle mechanism (not shown) transmit current to and from the distal forceps 110. A rigid tilt rod 116 pivotably connects to an eyelet 118 at the upper proximal edge of the tilt control member 106. Longitudinal movement of the tilt rod 116 causes the tilt control member 106 to pivot about the pins 108, thus tilting the distally extended forceps 110, as shown in FIG. 12. From the angled orientation of FIG. 12, the forceps 110 may be brought back into alignment with the tubular sheath 100 by pulling on the tilt rod 116 from the handle end.

Referring to FIGS. 11–14, the forceps 110 include half cone-shaped camming members 120 mounted such that their flat sides 122 face each other across a gap 124 created by the normal outward bias of the forceps. A coagulation control sleeve 126 surrounds the two camming members 120, providing a means for closing the distal forceps tips 112. In this respect, the sleeve 126 slides longitudinally over the camming members 120 in a distal direction to close the forceps tips 112, and releases the tips when slid in a proximal direction due to the outwardly biased mounting of the forceps 110. A pair of closed loop control wires 128a,b, one on each lateral side, apply linear displacement forces to the sleeve 126, causing movement back and forth over the camming members 120. Each control wire 128 attaches to the coagulation sleeve 126 and extends in both the proximal and distal directions. Each distally directed wire segment looping around an eyelet 130 on a camming member to join the proximally directed wire segment which loops around a first shaft 132 in the proximal handle mechanism. Tension in the distally extending segment of the control wires 128a,b tends to displace the coagulation sleeve 126 distally to close the forceps tips 112. Conversely, tension in the distally extending segment of the control wires 128a,b retracts the sleeve 126 proximally over the camming members 120 and allows the forceps tips 112 to open.

As seen in FIG. 12, the first control wires 128a,b extend through the tilt control member 106, dividing the control wires into proximal and distal lengths, the proximal lengths extending from the tilt control member to the handle and the distal lengths extending from the tilt control member to the camming members. In the angled position of FIG. 12, the proximal lengths of wire remain aligned axially, while the distal lengths of wire form an angle with the axis of the tubular sheath, the flexibility inherent in the wires 128 allowing such a bend at the tilt control member.

A cleaning rod 134 may be slid longitudinally along the forceps 110 via a second pair of control wires 136a,b, in a similar manner as the displacement mechanism for the coagulation sleeve 126. The cleaning rod 134 includes an elongated shaft portion 138 with a cleaning tip 140 disposed at the distal end after a 90° bend 142. The cleaning rod 134 also includes a proximal guide member 144 arranged concentrically around the forceps 110. The distal cleaning tip 140 is normally disposed between the camming members 120 and may be extended distally to reach the forceps tips 112 for cleaning purposes. The second pair of control wires 136 loops around a second actuation shaft 146 at the handle (not shown) to extend distally through the tilt control member 106 and attach to a lateral side of the guide member 144, and thereafter through a pulley or eyelet 148 at the distal end of the camming members 120. Rotation of the second actuating shaft 146 causes the cleaning rod 134 to slide longitudinally along the electrocautery forceps 110.

To more clearly describe the first pair of control wires 128a,b and coagulation sleeve displacement, FIG. 13 shows a top view of the coagulation device 10 without the second pair of control wires 136a,b removed. Both of the first pair of control wires 128a,b loops around identically sized pulleys 150 keyed to the first shaft 132, and thus rotation of the first shaft displaces both wires equally in two longitudinal directions. The wires 128a,b extend through a group of four apertures 152 in the tilt control member 106, shown in the upper half of FIG. 15. The apertures 152 are sized to allow free sliding movement of the wires 128a,b therethrough and are preferably rounded at each end to reduce frictional wear on the contacting surfaces when the tilt control member 106 pivots. The first pair of control wires 128a,b continue distally, one end of each wire terminating at the coagulation control sleeve 126, and the other end looping around the eyelet 130 at the upper distal edge (see also FIG. 12) of the camming members before also terminating at the sleeve. As will be apparent, rotation of the first shaft 132 in one direction creates tension in the control wires 128a,b on one or the other side of the sleeve 126 allowing the sleeve to be manipulated in both directions remotely from the handle.

With reference to the cleaning rod 134 displacement mechanism, FIG. 14 shows a top view of the coagulation device 10 with the first pair of control wires 128a,b removed. Both of the second pair of control wires 136a,b loop around identically sized pulleys 154 keyed to the second shaft 146, and thus rotation of the second shaft displaces both wires equally in two longitudinal directions. The wires 136a,b extend through a group of four apertures 156 in the tilt control member 106, shown in the lower half of FIG. 15. The apertures 156 are sized to allow free sliding movement of the wires 136a,b therethrough and are preferably rounded at each end to reduce frictional wear on the contacting surfaces when the tilt control member 106 pivots. The second pair of control wires 136a,b continue distally, one end of each wire terminating at the cleaning rod guide member 144, and the other end looping around the eyelet 148 at the middle distal edge (see also FIG. 12) of the camming members 120 before also terminating at the guide member. As will be apparent, rotation of the second shaft 146 in one direction creates tension in the control wires 136a,b on one or the other side of the guide member 144 allowing the guide member to be manipulated in both directions from the handle.

In operation, the coagulation device 10 is typically guided to a treatment site within an outer cannula, the distal electrocautery forceps 110 extending from the cannula. The forceps tips 112 may be open or closed during the insertion procedure and are subsequently positioned so that an area of tissue to be cauterized is between the tips. The first shaft 132 rotates in a first direction to transmit longitudinal movement to the coagulation sleeve 126 in a distal direction, closing the tips 112 about the tissue. A predetermined current passes through the conducting leads 114 and through the forceps 110 to close the circuit at the extreme distal tips 112, generating heat to cauterize the tissue. The first shaft 132 then rotates in a second direction to pull the sleeve proximally to the narrow portion of the camming members 120, allowing the natural spring bias of the forceps 110 to open the tips 112. At this point, the second shaft 146 rotates in one direction to transmit longitudinal movement to the cleaning rod 134, causing the cleaning tip 140 to scrape any residual, tissue from the inner, top and bottom edges of the forceps tips 112. The cleaning rod 134 is retracted by rotation of the second shaft 146 in a direction opposite the first. The coagulation procedure has thus been completed and the device 10 may be repositioned to treat a separate area.

To access an area of tissue which may be obscured by an anatomical obstruction, the forceps 110 may be tilted to form an angle with the tubular sheath 100 longitudinal axis. Movement of the tilt rod 116 in a distal direction causes the tilt control member 106 to pivot about the pins 108. The entire apparatus distal from the tilt control member 106 thus pivots out of the aperture 102 in the side of the sheath 100. At a certain angle of pivot, the forceps 110 are again brought together about an area of tissue to be cauterized. The procedure for cautery resembles exactly the procedure as describe above with the forceps 110 aligned with the sheath 100. The control wires 128, 136 function in the same manner as before, the sleeve 126 and cleaning rod 134 being fully operational with the forceps 110 in the angled position. After the cautery procedure, the tilt rod 116 retracts in the proximal direction to return the forceps 110 to a longitudinally aligned position for withdrawal of the coagulation device 10 from the cannula.

Although certain embodiments and examples have been used to illustrate and describe the present invention, it is intended that the scope of the invention not be limited to the specific embodiments set forth herein. Accordingly, the scope of the invention is intended to be defined only by the claims which follow.

We claim:

1. An endoscopic bipolar coagulation device, comprising:
    an elongate sheath having a distal end and a proximal end, said distal end being insertable into a body of a mammal;
    an electrocautery forceps comprising a pair of electrically conductive rods extending through and inside the sheath from the proximal end to the distal end, each of said rods terminating at its distal end in a tip having an inner surface and an outer surface; and
    a cleaner comprising a rod extending through and inside the sheath, the distal end of said rod having a tip shaped to conform to the inner surface of the tips of the forceps.

2. The coagulation device of claim 1, wherein said electrically conductive rods and said sheath are slidable relative to one another, and wherein said device further comprises a wedge on at least one of said electrically conductive rods, said wedge being positioned proximally behind the tip of said electrically conductive rod, whereby upon relative sliding motion of the electrically conductive rods toward the distal end of the sheath, said wedge acts as a cam which causes the tips of the forceps to be brought together.

3. The coagulation device of claim 2, wherein said relative sliding motion comprises the sliding movement of the sheath toward the distal end of the electrically conductive rods.

4. The coagulation device of claim 2, wherein said relative sliding motion comprises the sliding movement of the electrically conductive rods toward the proximal end of the sheath.

5. The coagulation device of claim 1, wherein each of said electrically conductive rods terminates at its distal end in a rounded tip.

6. The coagulation device of claim 1, wherein each of said electrically conductive rods terminates at its distal end in a tip having a flat tissue contacting surface.

7. The coagulation device of claim 1, wherein said tips of said electrically conductive rods are comprised of an alloy comprised of from 4.75% to 15.5% silver, 0.01% to 7.5% phosphorous, and 77.0% to 95.24% copper.

8. The coagulation device of claim 7, wherein said tips of said electrically conductive rods are comprised of an alloy comprised of 80% copper, 15% silver, and 5% phosphorous.

9. The coagulation device of claim 1, wherein said tip of said cleaner is comprised of plastic.

10. The coagulation device of claim 1, wherein said tip of said cleaner is comprised of metal.

11. The coagulation device of claim 1, further comprising means for pivoting the forceps to an angularly disposed position relative to the sheath.

12. A method of coagulating internal tissue of a mammal using a device of the type comprising a sheath, an electrocautery forceps having tips at the distal ends thereof, and a wedge on at least one arm of the forceps, comprising:
   inserting said device into an internal portion of the mammal;
   placing the tips of the forceps on opposite sides of the internal tissue;
   bringing the tips of the forceps together upon relative motion of the rods toward the proximal end of the sheath;
   activating an electrical current; and
   cleaning the tips of the forceps inside the mammal, using a cleaner comprising a rod extending through and inside the length of the sheath, the distal end of said rod having a tip configured to track the tips of the forceps, by sliding the tip of the cleaner along the tips of the forceps at least once.

13. The method of claim 12, further comprising bringing the tips of the forceps together upon relative motion of the rods toward the proximal end of the sheath prior to the cleaning of the tips.

14. The method of claim 12, further comprising bending the tips of the forceps inside the mammal, using a means for pivoting the forceps into an angularly disposed position relative to the sheath.

15. A method of coagulating internal tissue of a mammal using a device of the type comprising a sheath, an electrocautery forceps having tips at the distal ends thereof, a wedge on at least one arm of the forceps, and a means for pivoting the forceps comprising:
   inserting said device into an internal portion of the mammal;
   bending the tips of the forceps using said means for pivoting the forceps into an angularly disposed position relative to the sheath;
   placing the tips of the forceps on opposite sides of the internal tissue;
   bringing the tips of the forceps together by displacing a sleeve surrounding said forceps along said wedge; and
   activating an electrical current.

16. The method of claim 15, further comprising cleaning the tips of the forceps inside the mammal, using a cleaner comprising a rod extending through and inside the length of the sheath, the distal end of said rod having a tip configured to track the tips of the forceps, by sliding the tip of the cleaner along the tips of the forceps at least once.

17. The method of claim 16, further comprising bringing the tips of the forceps together by displacing said sleeve prior to the cleaning of the tips.

* * * * *